(12) United States Patent
Jaillet

(10) Patent No.: US 10,350,232 B1
(45) Date of Patent: Jul. 16, 2019

(54) MEDICINAL DROPS

(71) Applicant: Peter D. Jaillet, Lewisville, TX (US)

(72) Inventor: Peter D. Jaillet, Lewisville, TX (US)

( * ) Notice: Subject to any disclaimer, the term of this patent is extended or adjusted under 35 U.S.C. 154(b) by 67 days.

(21) Appl. No.: 14/527,870

(22) Filed: Oct. 30, 2014

Related U.S. Application Data

(60) Provisional application No. 61/899,524, filed on Nov. 4, 2013.

(51) Int. Cl.
| | | |
|---|---|---|
| *A61K 31/717* | (2006.01) |
| *A61K 31/7004* | (2006.01) |
| *A61K 31/69* | (2006.01) |
| *A61K 49/00* | (2006.01) |

(52) U.S. Cl.
CPC ............ *A61K 31/717* (2013.01); *A61K 31/69* (2013.01); *A61K 31/7004* (2013.01); *A61K 49/00* (2013.01)

(58) Field of Classification Search
CPC .. A61K 31/717; A61K 49/00; A61K 31/7004; A61K 31/69
See application file for complete search history.

(56) References Cited

U.S. PATENT DOCUMENTS

| | | |
|---|---|---|
| 4,409,205 A | 10/1983 | Shively |
| 6,153,582 A | 11/2000 | Skelnik |
| 7,128,928 B2 | 10/2006 | Singh et al. |
| 7,732,425 B2 | 6/2010 | Matsuo et al. |
| 7,858,582 B2 | 12/2010 | Jin et al. |
| 7,960,350 B2 | 6/2011 | Robledo |
| 8,298,581 B2 | 10/2012 | Fischer et al. |
| 2002/0055486 A1* | 5/2002 | Matsuo ................ A61K 9/0048 514/53 |
| 2009/0048188 A1* | 2/2009 | Matsuo ................ A61K 31/375 514/35 |

FOREIGN PATENT DOCUMENTS

WO WO2008077110 A2 * 6/2008

OTHER PUBLICATIONS

Brown, et al, "The Preservation of Ophthalmic Preparations", J. Soc. Cosmetic Chemists, 16, 369-393 (1965).
Houlsby, et al. "Antimicrobial Activity of Borate-Buffered Solutions" Antimicrobial Agents and Chemotherapy, May 1986, vol. 29, No. 5, pp. 803-806.

* cited by examiner

*Primary Examiner* — Robert S Cabral
(74) *Attorney, Agent, or Firm* — Edwin S. Flores; Daniel J. Chalker; Chalker Flores, LLP

(57) ABSTRACT

The present invention includes a concentration of at least 7.5% w/w saccharide other than trehalose, a preservative, in a buffered solution, wherein the composition is formulated for optic or otic administration. In certain embodiments, the composition is used to treat dry eyes, presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, multiple sclerosis, Parkinson's disease, Alzheimer's disease, attention deficit disorder, attention deficit hyperactivity disorder, or Guillain-Barre syndrome.

32 Claims, No Drawings

MEDICINAL DROPS

CROSS-REFERENCE TO RELATED APPLICATIONS

This application claims priority to U.S. Provisional Application Ser. No. 61/899,524, filed Nov. 4, 2013, the entire contents of which are incorporated herein by reference.

TECHNICAL FIELD OF THE INVENTION

The present invention relates in general to the field of medicinal drops, and more particularly, to novel compositions for the treatment of medical conditions for treating eye and ear conditions.

STATEMENT OF FEDERALLY FUNDED RESEARCH

Not Applicable.

INCORPORATION-BY-REFERENCE OF MATERIALS FILED ON COMPACT DISC

Not Applicable.

BACKGROUND OF THE INVENTION

Without limiting the scope of the invention, its background is described in connection with medicinal drops.

U.S. Pat. No. 4,409,205 is directed to an ophthalmic aqueous solution having an ionic salt ion content within the range 0.01% to 7.5% expressed as sodium chloride equivalents and comprising a non-ionic synthetic polymer such as polyvinyl alcohol and/or polyethylene glycol, and a non-ionic tonicity adjusting agent. The solution is effective in treating "dry eye" conditions by causing a normalization of irregularly structured tears and at least retarding the precipitation of protein-like substances from the aqueous layers thereof.

U.S. Pat. No. 6,153,582, is directed to a defined serum-free medical solution for applications in Ophthalmology, that contains one or more cell nutrient supplements, and a growth factor(s) which maintains and enhances the preservation of eye tissues, including human corneal, retinal and corneal epithelial tissues at low to physiological temperatures.

U.S. Pat. No. 7,128,928, is directed to an ophthalmic formulation with novel gum composition, specifically, a pharmaceutical composition suitable for topical administration to an eye, the composition comprising (a) a pharmacologically effective concentration of an active agent; and (b) a combination of at least two ophthalmically compatible polymers comprising a novel gum system. In preferred embodiments of the present invention, the compositions increase the retention time of the active agent in the eye, when compared to compositions with other gums or gum systems.

U.S. Pat. No. 7,858,582 is direct to an ophthalmic hGM-CSF preparation, specifically, an external preparation and the method for produce the same, in which said external preparation comprises recombinant human growth hormone or recombinant human granulocyte macrophage colony-stimulating factor and pharmaceutical acceptable carriers. The present invention also relates to application and usage method in preparing medicaments for treatment of various lesions and ulcers, especially corneal lesions and corneal ulcers.

U.S. Pat. No. 7,960,350 is directed to a composition and method for the treatment of eye disease, specifically, methods of preventing and/or ameliorating one or more symptoms associated with an eye disease such as dry eye syndrome, cataracts of the eye and nuclear sclerosis of the eye lens by administering to a subject a therapeutically effective amount of N-$\alpha$-acetyl-L-histidine.

United States Patent Application Publication No. 2003/0186931 is directed to a pharmaceutical composition for ophthalmic use, specifically, it describes an ophthalmic pharmaceutical composition comprising trehalose as an effective ingredient and a pharmaceutically-acceptable carrier. The pharmaceutical composition is a safe, long-term continuously-administrable, therapeutic and/or prophylactic agent for the ophthalmologic clinical symptoms and signs in Sjogren syndrome.

United States Patent Application Publication No. 2007/0042044 is directed to a matrix compositions for controlled delivery of drug substances, specifically, a controlled release pharmaceutical composition for oral use is provided in the form of a coated matrix composition, the matrix composition comprising: i) a mixture of a first and a second polymer that have plasticizing properties and which have melting points or melting intervals of a temperature of at the most 200° C., the first polymer being selected from the group consisting of polyethylene glycols and polyethylene oxides, and the second polymer being selected form block copolymer of ethylene oxide and propylene oxide including poly (ethylene-glycol-b-(DL-lactic acid-co-glycolic acid)-b-ethylene glycol (PEG-PLGA PEG), poly((DL-lactic acid-co-glycolic acid)-g-ethylene glycol) (PLGA-g-PEG), poloxamers and polyethylene oxide-polypropylene oxide (PEO-PPO); ii) a therapeutically, prophylactically and/or diagnostically active substance, the matrix composition being provided with a coating having at least one opening exposing at one surface of said matrix, wherein the active substance is released with a substantially zero order release.

Brown et al, The Preservation of Ophthalmic Preparation, J. Soc. Cosmetic Chemists 16 pp. 369-393 (1965), states that the U.S. National Formulary recommends a 2% boric acid solution as a general ophthalmic vehicle and states that the U.S. Pharmacopoeia XV recommends an isotonic phosphate buffer as an ophthalmic vehicle in addition to boric acid solution. It is said that most of the common ophthalmic drugs can be autoclaved in 2% boric acid solution without seriously affecting their therapeutic activity.

Houlsby et al, Antimicrobial Activity of Borate-Buffered Solutions, Antimicrobial Agents and Chemotherapy, May 1986, pp. 803-806, teaches that borate-buffered solutions exhibit antimicrobial activity and are suitable for use as a generic vehicle for ophthalmic pharmaceutical agents.

SUMMARY OF THE INVENTION

The present invention includes a composition comprising a concentration of at least 15% w/w of a saccharide other than trehalose, a preservative, in a buffered solution, wherein the composition is formulated for optic or otic administration. In one aspect, wherein the buffered solution is an aqueous phosphate-buffered solution comprising monobasic sodium phosphate and dibasic sodium phosphate. In another aspect, the buffered solution is an aqueous phosphate-buffered solution comprising monobasic sodium phosphate in a concentration of 0.01 to 0.1% w/w and dibasic sodium phosphate in a concentration of 0.01 to 0.1% w/w. In another aspect, the composition further comprises a sodium chloride, or a potassium chloride salt. In another aspect, the saccharide is, e.g., dextrose or galactose, or is a disaccharide that is selected from, e.g., at least one of sucrose, maltose, or lactose, and is at a concentration of at least one of 7.5%, 10%, 15%, 16%, 17%, 18%, 19%, 20%, 25%, 29%, 30%, 31%, 32%, 33%, 34%, 35%, 40%, 45%, or 50% w/w, 20 to 30% w/w, 25 to 35% w/w, 30 to 35% w/w, 7.5% to 50% w/w, greater that 30% up to 45%, between 30% and 45% w/w, and up to 50% w/w. In another aspect, the preservative comprises at least one of borate, boric acid, sodium borate, or potassium borate. In another aspect, the composition further comprises a viscosity modifier.

In one embodiment the invention is an ophthalmic or otic composition consisting essentially of at least 7.5% w/w of a saccharide other than trehalose, boric acid, and a buffered solution. In another embodiment the invention is an ophthalmic or otic composition consisting of at least 7.5% dextrose and a preservative, in a buffered solution. In one aspect, the buffered solution is an aqueous phosphate-buffered solution comprising monobasic sodium phosphate in a concentration of 0.01 to 0.1% w/w and dibasic sodium phosphate in a concentration of 0.01 to 0.1% w/w. In another aspect, the viscosity modifier is sodium carboxymethylcellulose is at a concentration of 0.005 to 0.05% w/w. In another aspect, the dextrose is at a concentration of at least one of 7.5%, 10%, 15%, 16%, 17%, 18%, 19%, 20%, 25%, 29%, 30%, 31%, 32%, 33%, 34%, 35%, 40%, 45%, or 50% w/w, 20 to 30% w/w, 25 to 35% w/w, 30 to 35% w/w, 7.5% to 50% w/w, greater that 30% up to 45%, between 30% and 45% w/w, and up to 50% w/w. In another aspect, the boric acid is at a concentration of 0.01 to 0.1% w/w. In another embodiment, the ophthalmic or otic composition consists of at least 30% w/w sucrose and boric acid, in a buffering solution.

Another embodiment of the present invention includes a method of making an ophthalmic or otic composition consisting essentially of: providing dextrose at at least 7.5% w/w; providing a viscosity modifier; providing boric acid; providing a buffered solution; and combining the viscosity modifier, the sucrose, the boric acid, and the buffered solution. In one aspect, the buffered solution is an aqueous phosphate-buffered solution comprising monobasic sodium phosphate and dibasic sodium phosphate. In another aspect, the viscosity modifier is sodium carboxymethylcellulose and is at a concentration of 0.0005 to 0.005% w/w, 0.005 to 0.05% w/w, or 0.05 to 0.5% w/w. In another aspect, the dextrose is in a concentration of at least one of 7.5%, 10%, 15%, 16%, 17%, 18%, 19%, 20%, 25%, 29%, 30%, 31%, 32%, 33%, 34%, 35%, 40%, 45%, or 50% w/w, 20 to 30% w/w, 25 to 35% w/w, 30 to 35% w/w, 7.5% to 50% w/w, greater that 30% up to 45%, between 30% and 45% w/w, and up to 50% w/w. In another aspect, the boric acid is at a concentration of 0.001 to 0.01% w/w, 0.01 to 0.1% w/w, or 0.1 to 1% w/w.

Yet another embodiment of the present invention includes a method of treating a medical condition, disease or disorder comprising: identifying a subject in need of treatment for a medical condition; and applying a ophthalmic or otic composition to the eye or the ear, the ophthalmic or otic composition comprising at least 7.5% w/w of a saccharide, a preservative, and a buffered solution. In one aspect, the medical condition, disease or disorder is selected from at least one of presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, multiple sclerosis, Parkinson's disease, Alzheimer's disease, attention deficit disorder, attention deficit hyperactivity disorder, or Guillain-Barre syndrome. In another aspect, the buffered solution is an aqueous phosphate-buffered solution comprising monobasic sodium phosphate and dibasic sodium phosphate. In another aspect, the sodium carboxymethylcellulose is at a concentration of 0.005 to 0.05% w/w. In another aspect, the saccharide is, e.g., dextrose or galactose, or is a disaccharide that is selected from, e.g., at least one of sucrose, maltose, or lactose, and is in a concentration of at least one of 7.5%, 10%, 15%, 16%, 17%, 18%, 19%, 20%, 25%, 29%, 30%, 31%, 32%, 33%, 34%, 35%, 40%, 45%, or 50% w/w, 20 to 30% w/w, 25 to 35% w/w, 30 to 35% w/w, 7.5% to 50% w/w, greater that 30% up to 45%, between 30% and 45% w/w, and up to 50% w/w. In another aspect, the boric acid is at a concentration of 0.01 to 0.1% w/w. In another aspect, the medical condition is not Sjogren syndrome. In one aspect, the saccharide is not trehalose, and is selected from at least one of dextrose, galactose, sucrose, maltose, or lactose.

Yet another embodiment of the present invention includes a method of treating a medical condition, comprising: identifying a patient with the medical condition; and providing the patient with an effective amount of a composition comprising a concentration of at least 19% w/w of a saccharide other than trehalose and a preservative, in a buffered solution sufficient to improve the medical condition. In one aspect, the medical condition is selected from at least one of presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, multiple sclerosis, Parkinson's disease, Alzheimer's disease, attention deficit disorder, attention deficit hyperactivity disorder, Guillain-Barre syndrome, deep pain, speech disorders, autism spectrum disorders, or inability to speak. In another aspect, the medical condition is not an autoimmune condition or disease. In another aspect, the medical condition is not Sjogren syndrome.

Yet another embodiment of the present invention includes a method of evaluating a candidate drug believed to be useful in treating a medical condition, the method comprising: a) measuring the extent of the medical condition from a set of patients other than Sjorgen's syndrome; b) administering a candidate drug comprising a composition having a concentration of at least 7.5% w/w saccharide, a preservative, in a buffered solution to a first subset of the patients, and a placebo to a second subset of the patients, wherein the candidate drug comprises a concentration of at least 7.5% w/w of the saccharide, a preservative, in a buffered solution; c) repeating step a) after the administration of the candidate drug or the placebo; and d) determining if the candidate drug improves the medical condition in the patient that is statistically significant as compared to any reduction occurring in the second subset of patients, wherein a statistically significant reduction indicates that the candidate drug is useful in treating the medical condition. In one aspect, the saccharide is, e.g., dextrose or galactose, or is a disaccharide that is selected from, e.g., at least one of sucrose, maltose, or lactose, and is in a concentration of at least one of 7.5%, 10%, 15%, 16%, 17%, 18%, 19%, 20%, 25%, 29%, 30%, 31%, 32%, 33%, 34%, 35%, 40%, 45%, or 50% w/w, 20 to 30% w/w, 25 to 35% w/w, 30 to 35% w/w, 7.5% to 50% w/w, greater that 30% up to 45%, between 30% and 45% w/w, and up to 50% w/w. In another aspect, the medical condition is selected from Presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, multiple sclerosis, Parkinson's disease, Alzheimer's disease, attention deficit disorder, attention deficit hyperactivity disorder, Guillain-Barre syndrome, deep pain, speech disorders, autism spectrum disorders, inability to speak.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present inventor has found the need for novel compositions to treat a number of medical conditions related to optical and auditory diseases or conditions. The present inventor sought to design a composition that could be used in all patients for a variety of conditions. Surprisingly, although originally designed to provide improved compositions for the treatment of dry eye and related conditions, it became apparent after a number of additional improvements that the composition was able to provide additional medical benefits, including a wide variety of neurological conditions or conditions related to mental concentration, cognition, presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, attention deficit hyperactivity disorder, or Guillain-Barre syndrome. The present invention works on patients whether or not they have an underlying autoimmune condition.

Yet another aspect of the present invention includes the improvements to medical conditions or diseases that it was able to accomplish when used in the ear. The same composition was used otically with surprising results. By applying as drop in one or more of the ears of a number of subjects, the present invention provided remarkable improvement in symptoms associated with deep pain, speech disorders, autism spectrum disorders, and a subject's inability to speak.

The present invention include a composition that includes 15 to 50% weight-to-weight (w/w) sucrose, a preservative and a buffering agent, wherein the composition is in solution and is adapted for use in the eye or ear. In certain embodiments, the saccharide or disaccharide (other than trehalose) is at at least one of 7.5%, 10%, 15%, 16%, 17%, 18%, 19%, 20%, 25%, 29%, 30%, 31%, 32%, 33%, 34%, 35%, 40%, 45%, or 50% w/w, 20 to 30% w/w, 25 to 35% w/w, 30 to 35% w/w, 7.5% to 50% w/w, greater that 30% up to 45%, between 30% and 45% w/w, and up to 50% w/w. The saccharide can be, e.g., dextrose or galactose, or is a disaccharide that is selected from, e.g., at least one of sucrose, maltose, or lactose, which can be D- or L-sugars, but not trehalose. The buffered solution can be any of a number of buffers, e.g., an aqueous phosphate-buffered solution comprising monobasic sodium phosphate and dibasic sodium phosphate. In certain embodiments, aqueous phosphate-buffered solution comprising monobasic sodium phosphate in a concentration of 0.01 to 0.1% w/w and dibasic sodium phosphate in a concentration of 0.01 to 0.1% w/w. In certain embodiments, the preservative can be preservative comprises at least one of borate, boric acid, sodium borate, or potassium borate. In one variant, the sucrose of the present invention can be substituted with lactate, e.g., sodium lactate.

In operation, the composition can be made by dissolving sucrose in water, with or without heating and then the pH of the composition can be brought to around pH 7.0 with one or more buffers. Next, the preservative can be added to the composition. In certain other embodiment, the sucrose can be dissolved directly into a previously buffered solution, which may also include the preservative.

The present invention has been tested for allergic eye conditions and it has been found that the present invention provided substantially less irritation when compared to currently available over-the-counter eye drops in over 120 subjects. The present invention has been tested for scratchy eye on over 120 subjects with improved results. The composition was tested on a similar amount of males and females. To date, over 300 subjects have seen a positive response to the composition of the present invention. The composition has been tested with an age range that included subjects from 4 years to late 70's, again, with equal numbers of male and female subjects. Thus, the present invention can be used from pediatric to seasoned individuals.

The present invention is particularly suitable for making small, medium, large, and very large mixtures, e.g., 5, 10, 50, or 100 ml, or 1, 5, 10, 50, 100, 200, 500, 1,000, 3,000 or even 5,000 liters. As will be apparent to those of skill in the art, the actual amount of the saccharide may be varied in accordance with the dissolution characteristics of the saccharide, which may be further varied by addition of agents that affect the solubility and/or dissolution of the active in, e.g., water. As regards a pediatric formulation, the amount of active may be reduced in accordance with the dosage form approved for pediatric use.

In one example of the present invention, for delivery of 5 milliliters, the saccharide is dissolved into, e.g., double deionized, USP water. Next, additives are added, e.g., the viscosity modifier, preservatives (if any), and buffering agent(s). In one example, the additives are sodium carboxymethylcellulose, sodium carboxymethylcellulose, and the buffer is a phosphate buffer. The additives are then added to water and blended together for about 1 to 120 minutes (e.g., between about 5, 10, 20, 25, 30, 35, 40, 45, 50, 55, 60, 65, 70, 75, 80, 85, 90, 95, 100, 110, and 120 minutes). The saccharide, excipient and additives are then blended together for about 1 to 60 minutes (e.g., between about 5, 10, 15, 20, 25, 30, 35, 40, 45, 50, 55 and 60 minutes). Examples of excipients for liquid formulations include microcrystalline cellulose, powdered cellulose, precipitated calcium carbonate, sorbitol, calcium sulfate, and others known to those of ordinary skill in the art.

This process is particularly suitable for very large mixtures, e.g., 500, 1,000, 3,000 or even 5,000 liters. As will be apparent to those of skill in the art, the actual amount of the partially-excipient soluble active salt (e.g., non- or partially-water soluble) may be varied in accordance with the dissolution characteristics of the active, which may be further varied by addition of agents that affect the solubility and/or dissolution of the active in solution, e.g., water. As regards a pediatric formulation, the amount of active may be reduced in accordance with the dosage form approved for pediatric use. A batch was prepared with the following components:

| Components | Weight |
|---|---|
| Dextrose (USP) | 7.25 kg |
| Sodium carboxymethylcellulose | 0.25 kg |
| Boric acid | 0.8 kg |
| Sodium Phosphate, Monobasic | 1.725 kg |
| Sodium Phosphate, dibasic | 1.775 kg |
| Purified water (USP) | qs to 25 kg |

In another example, two different saccharides are delivered in a liquid form for mixed release. In order to produce an acceptable release and physiologic profile, two different actives are delivered in a single liquid formulation. The saccharide used in these examples included dextrose at 29% weight-to-weight. One source of dextrose is dextrose obtained from beet sugar. The dextrose can be substituted with sucrose, maltose, and/or lactose.

Over 10 subjects have been provided the present invention to improve neurological health, which include subjects with traumatic brain injury, with positive results for clarity of the thought process, better dream states, and increased color awareness.

The following are specific examples of the use of the present invention for optic use, including basic results obtained with the same.

Example 1

50-year old female presbyopia. S/p LASIK. Near vision for reading and tv 70 percent better after eye drops. Changes within 10 seconds.

Example 2

45-year old male with presbyopia. Night vision and reading decline. 80% improvement with reading. Subject had 50% better night vision.

Example 3

70-year old female with unilateral eye pain. 90% resolution within 10 seconds. Resolved as long as daily usage.

Example 4

40-year old female with blurry vision within ten feet daily. Occurs daily for four hours. Application of the composition clears vision 70% improvement with daily application. So good that patient does not need prescription lenses in a.m.

Example 5

23-year old female that complains of dry eyes, and foggy thought process, 1 drop 2× daily in one week dramatic improvement of vision and clearer thoughts.

Example 6

21-year old male, dry scratchy eyes, 1 drops 2× daily, eyes feels like they have been waxed.

Example 7

55-year old male, dry eyes, confused mental function, 1 drop 2× daily, in one week eyes feel great with a better ability to think through daily function.

Example 8

33-year old female with left eye scotoma measuring 254 mm, post eye drops physiological blind spot decreased to 141 mm.

Example 9

33-year old female with left eye scotoma measuring 141 mm after one drop each eye, one week later, using the composition twice daily, scotoma now measures 121 mm. Vision is also clearer and colors are more colorful.

Example 10

50-year old female with scratchy blurring vision, post eye drops vision improved and scratchy blurry eyes are doing great.

Example 11

53-year old female with past Lasik, suffers with allergy eyes that are sensitive to all environmental allergy, since using the composition now she is able to go outside and enjoy the outdoors.

Example 12

60-year old female. One week on eye drops, Far vision went from −5 to −475 amazing. Cravings for sugar gone first time in 10 years, better at video games for hand eye coordination. Played game over a year and following the treatment it was the first time she beat the game.

Example 13

56-year old male, diabetic with noticeable changes in vision, thought process very difficult to stay on task. After 4 weeks on the composition, mindset has totally changed, with improved cognitive function and a clearer ability to see colors.

Example 14

42-year old female that had a grade 3 scratch of the sclera and an internal lid abrasion, saw optometrist and had a bandage and steroid crème, no resolve of the abrasion, day 2 after medical attention, saw the patient and applied 1 drop in both eyes immediate resolution of the abrasion feeling in the eye. Used the composition 1 drop 2-3× daily as needed in one week patient was totally healed and no negative feelings and able to see the colors better than prior.

Example 15

56-year old female with blocked tear duct, 1 drop 2× daily for 1 week, tear duct open and normal function has returned.

Example 16

70-year old male with DYT1 gene malfunction, global essential tremor, used the composition 1 drop 2× daily, slowing down of the frequency of the tremor.

Example 17

76-year old female with dry scratchy eyes, used the composition 1 drop 2× daily in one week eyes are feeling better than they have in years.

Example 18

19-year old male, traumatic brain injury, grade 3 concussion, vision and HI cognitive changes occurring, loss of memory and depressed and confused, 1 drop 2× daily, after 2 weeks clarity of thought improved. Vision has dramatically improved, depression lifting with better choices being made.

Example 19

24 year old male with 2 temporal lobe concussions, memory and good choices are problematic, bad dreams, and difficulty in moving. Used the composition 1 drop 2× daily after 2 weeks sleeping better with normal dreams. Better choices being make and stability of motor function has been noticed.

Example 20

69-year old that has vertigo, used the composition 1 drop 2× daily after 1 week balance has improved greatly.

Example 21

26-year old female with traumatic brain injury, cognitive losses are the biggest concern, used the composition 1 drop 2× daily there has been a noticeable difference in the ability to remember both task and daily habits.

Example 22

11-year old male with Attention deficit hyperactivity disorder (ADHD), compulsivity, and inability to maintain task. Used the composition 1 drop 2× daily has seen a magnificent change in behavior and compulsiveness.

Example 23

49-year old male diagnosed with Guillain-Barre syndrome, for 7 months, in a wheel chair as a quadriplegic, 1 drop both eyes day 1, able to move hand to take a bottle of water and with little assistance take a drink of the water. Used the composition 1 drop 2× daily, one week, able to feel from his knee to the ankle. Continual drops week 2, able to lift both arms to shoulder height. Week 3 now is marching in place while sitting in the wheel chair. Has feeling over the torso and arms and legs, still missing feeling in the feet.

Example 24

72-year old male with deep pain in his left leg, sharp and stinging. Used the composition 1 drop 2× daily after one week leg no longer has the sharp pains.

Example 25

22-year old male with dry eyes, used the composition 1 drop 2× daily, after 1 week eyes are feeling great with no signs of dryness.

Example 26

26-year old with dry eyes and allergy eyes. Used the composition 1 drop 2× daily, after one week eyes are not bother from the outside environment and feels eyes smooth and moist.

Example 27

44-year old male with dry eyes, used the composition 1 drop 2× daily, after 1 week eyes are feeling great with no signs of dryness.

The following are specific examples of the use of the present invention for otic use, including basic results obtained with the same.

Example 28

7-year old male with inability to pronounce "r's". Resolved with daily application of the composition on both ears.

Example 29

4-year old with cluttered speech disorders. Daily application of the composition increased fluency of speech.

Example 30

7-year old with Autism Spectrum Disorders (ASDs) including social deficiency. Used the composition one drop per ear daily. Use of the composition improved attention, facial responses and verbalization.

Example 31

5-year old boy with inability to speak, daily application of the composition to the ears, increased ability to speak as well, now speaking sentences.

Example 32

9-year old boy that has been mute since birth, daily drops of the composition to the ears and now is making many more sounds and beginning to say portions of words.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±0.5, 1, 2, 3, 4, 5, 6, 7, 8, 9, 10, 11, 12, 13, 14, 15% or even 20%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 4,409,205.
U.S. Pat. No. 6,153,582.
U.S. Pat. No. 7,858,582.
U.S. Pat. No. 7,960,350.
U.S. Pat. No. 7,128,928.
United States Patent Application Publication No. 2007/0042044.
United States Patent Application Publication No. 2003/0186931.
Brown et al, The Preservation of Ophthalmic Preparation, J. Soc. Cosmetic Chemists 16 369-393 (1965).
Houlsby et al, Antimicrobial Activity of Borate-Buffered Solutions, Antimicrobial Agents and Chemotherapy, May 1986, p. 803-806.

What is claimed is:

1. A composition comprising a mono or disaccharide, a preservative, in a buffered solution, wherein the composition is formulated for optic or otic administration, wherein the composition is free of trehalose, wherein the mono or disaccharide is at a concentration of at least one of greater than 30% up to 45%, or between 30% and 45% w/w.

2. The composition of claim 1, wherein the buffered solution is an aqueous phosphate-buffered solution comprising monobasic sodium phosphate and dibasic sodium phosphate.

3. The composition of claim 1, wherein the buffered solution is an aqueous phosphate-buffered solution comprising monobasic sodium phosphate in a concentration of 0.01 to 0.1% w/w and dibasic sodium phosphate in a concentration of 0.01 to 0.1% w/w.

4. The composition of claim 1, further comprising a sodium chloride, or a potassium chloride salt.

5. The composition of claim 1, wherein the mono or disaccharide is dextrose or galactose, or if a disaccharide is at least one of sucrose, maltose, or lactose.

6. The composition of claim 1, wherein the preservative comprises at least one of borate, boric acid, sodium borate, or potassium borate.

7. The composition of claim 1, further comprising a viscosity modifier.

8. The composition of claim 1, wherein the composition is specifically adapted for ophthalmic or otic use.

9. An ophthalmic or otic composition consisting essentially of a mono or disaccharide, boric acid, and a buffered solution, wherein the composition excludes trehalose, wherein the mono or disaccharide is at a concentration of at least one of greater than 30% up to 45%, or between 30% and 45% w/w.

10. An ophthalmic or otic composition consisting of dextrose and a preservative, in a buffered solution, wherein the composition excludes trehalose, wherein the dextrose is at a concentration of at least one of greater than 30% up to 45%, or between 30% and 45% w/w.

11. The ophthalmic or otic composition of claim 10, wherein the buffered solution is an aqueous phosphate-buffered solution consists of monobasic sodium phosphate in a concentration of 0.01 to 0.1% w/w and dibasic sodium phosphate in a concentration of 0.01 to 0.1% w/w.

12. The ophthalmic or otic composition of claim 10, wherein the buffer further consists of boric acid at a concentration of 0.01 to 0.1% w/w.

13. A composition consisting essentially of a concentration of at least 15% w/w mono or disaccharide, a preservative, in a buffered solution, wherein the composition is formulated for optic or otic administration and the mono or disaccharide is not trehalose.

14. An ophthalmic or otic composition consisting of sucrose and boric acid, in a buffering solution, wherein the sucrose is at a concentration of at least one of 31%, 32%, 33%, 34%, 35%, 40%, 45%, or 50% w/w, greater than 30% up to 45%, or between 30% and 45% w/w.

15. A method of making an ophthalmic or otic composition consisting essentially of:
providing a composition with a mono or disaccharide, wherein the composition excludes trehalose, wherein the mono or disaccharide is at a concentration of at least one of greater than 30% up to 45%, or between 30% and 45% w/w;
providing a viscosity modifier;
providing boric acid;
providing a buffered solution; and
combining the viscosity modifier, the boric acid, and the buffered solution into a single composition formulated for ophthalmic or otic administration, and wherein the mono or disaccharide is sucrose.

16. The method of making an ophthalmic or otic composition of claim 15, wherein the buffered solution is an aqueous phosphate-buffered solution comprising monobasic sodium phosphate and dibasic sodium phosphate.

17. The method of making an ophthalmic or otic composition of claim 15, wherein the viscosity modifier is sodium carboxymethylcellulose and is at a concentration of 0.0005 to 0.005% w/w, 0.005 to 0.05% w/w, or 0.05 to 0.5% w/w.

18. The method of making an ophthalmic or otic composition of claim 15, wherein the boric acid is at a concentration of 0.001 to 0.01% w/w, 0.01 to 0.1% w/w, or 0.1 to 1% w/w.

19. A method of treating an medical condition, disease or disorder of an eye or an ear comprising:
identifying a subject in need of treatment for a medical condition; and
applying an ophthalmic or otic composition to the eye or the ear, the ophthalmic or otic composition comprising a saccharide, a preservative, and a buffered solution, wherein the ophthalmic or otic composition excludes trehalose, wherein the saccharide is at a concentration of at least one of greater than 30% up to 45%, or between 30% and 45% w/w.

20. The method of claim 19, wherein the medical condition, disease or disorder is selected from at least one of dry eyes, presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, multiple sclerosis, Parkinson's disease, Alzheimer's disease, attention deficit disorder, attention deficit hyperactivity disorder, or Guillain-Barre syndrome.

21. The method of claim 19, wherein the buffered solution is an aqueous phosphate-buffered solution comprising monobasic sodium phosphate and dibasic sodium phosphate.

22. The method of claim 19, wherein the composition further comprises sodium carboxymethylcellulose at a concentration of 0.005 to 0.05% w/w.

23. The method of claim 19, wherein the saccharide is dextrose or galactose, or if a disaccharide is at least one of sucrose, maltose, or lactose.

24. The method of claim 19, wherein the composition further comprises boric acid at a concentration of 0.01 to 0.1% w/w.

25. The method of claim 19, wherein the medical condition is not Sjogren's syndrome.

26. A method of treating a medical condition, comprising:
identifying a patient with the medical condition; and
providing the patient with an effective amount of a composition consisting of a dextrose and a preservative, in a buffered solution sufficient to improve the medical condition, wherein the composition excludes trehalose, wherein the dextrose is at a concentration of at least one of greater than 30% up to 45%, or between 30% and 45% w/w.

27. The method of claim 26, wherein the medical condition is selected from at least one of dry eyes, presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, multiple sclerosis, Parkinson's disease, Alzheimer's disease, attention deficit disorder, attention deficit hyperactivity disorder, Guillain-Barre, deep pain, speech disorders, autism spectrum disorders, or inability to speak.

28. The method of claim 26, wherein the medical condition is not an autoimmune condition or disease or Sjorgen's syndrome.

29. A method of treating an medical condition, disease or disorder of an eye or an ear comprising:
identifying a subject in need of treatment for a medical condition other than Sjorgen's syndrome; and
applying a ophthalmic or otic composition to the eye or the ear, the ophthalmic or otic composition consisting of greater than 30% to 50% w/w mono or disaccharide, a preservative, and a buffered solution in an amount sufficient to treat the medical condition, disease or disorder.

30. A method of evaluating a candidate drug believed to be useful in treating a medical condition, the method comprising:
(a) measuring an extent of the medical condition from a set of patients excluding patients with Sjorgen's syndrome;
(b) administering a composition consisting of a candidate drug, and a placebo to a second subset of the patients, wherein the composition comprises a mono or disaccharide, a preservative, in a buffered solution, wherein the composition excludes trehalose, wherein the mono or disaccharide is at a concentration of at least one of greater than 30% up to 45%, or between 30% and 45% w/w;

(c) repeating step (a) after the administration of the candidate drug or the placebo; and (d) determining if the candidate drug improves the medical condition in the patient that is statistically significant as compared to any reduction occurring in a second subset of patients, wherein a statistically significant reduction indicates that the candidate drug is useful in treating the medical condition.

31. The method of claim 30, wherein the medical condition is selected from dry eyes, presbyopia, eye pain, blurred vision, confused mental function, scotoma, allergies, reduced craving for sugar, blocked tear ducts, tremors, vision and cognitive changes due to concussion, vertigo, TBI, loss of cognitive function as a result of traumatic brain injury, multiple sclerosis, Parkinson's disease, Alzheimer's disease, attention deficit disorder, attention deficit hyperactivity disorder, Guillain-Barre, deep pain, speech disorders, autism spectrum disorders, inability to speak.

32. The method of claim 30, wherein the monosaccharide is dextrose or galactose, or if a disaccharide is at least one of sucrose, maltose, or lactose, and is at a concentration of at least one of greater than 30% up to 45%, or between 30% and 45% w/w.

* * * * *